(12) United States Patent
Urban et al.

(10) Patent No.: US 12,352,855 B2
(45) Date of Patent: Jul. 8, 2025

(54) TIME-ALIGNED PLANE WAVE COMPOUNDING OF ULTRASOUND DATA

(71) Applicant: Mayo Foundation for Medical Education and Research, Rochester, MN (US)

(72) Inventors: Matthew W. Urban, Rochester, MN (US); Margherita Capriotti, San Diego, CA (US); James F. Greenleaf, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 343 days.

(21) Appl. No.: 18/044,185

(22) PCT Filed: Sep. 3, 2021

(86) PCT No.: PCT/US2021/049040
§ 371 (c)(1),
(2) Date: Mar. 6, 2023

(87) PCT Pub. No.: WO2022/051609
PCT Pub. Date: Mar. 10, 2022

(65) Prior Publication Data
US 2024/0027614 A1    Jan. 25, 2024

Related U.S. Application Data

(60) Provisional application No. 63/075,064, filed on Sep. 4, 2020.

(51) Int. Cl.
G01S 15/89    (2006.01)
A61B 8/00     (2006.01)
G01S 7/52     (2006.01)

(52) U.S. Cl.
CPC .......... G01S 15/8995 (2013.01); A61B 8/485 (2013.01); G01S 7/52022 (2013.01); G01S 7/52034 (2013.01)

(58) Field of Classification Search
None
See application file for complete search history.

(56) References Cited

U.S. PATENT DOCUMENTS 10,624,609 B2    4/2020   Greenleaf et al.
2014/0288428 A1* 9/2014   Rothberg ............ G01S 7/52047
                                              600/443

(Continued)

OTHER PUBLICATIONS

2020 IEEE International Ultrasonics Symposium. Final Program 2_0. Date Sep. 7, 2020-Sep. 11, 2020. Las Vegas, Nevada, USA. (Year: 2020).*

(Continued)

*Primary Examiner* — Isam A Alsomiri
*Assistant Examiner* — Jonathan D Armstrong
(74) *Attorney, Agent, or Firm* — Quarles & Brady LLP

(57) ABSTRACT

Shear wave elastography and/or other ultrasound imaging procedures are performed using a data acquisition technique in which data are acquired with high SNR while maintaining a high $PRF_e$, using conventional clinical ultrasound scanners. In general, ultrasound data are acquired using plane waves at different angles, after which a time alignment process is applied to the acquired data. The time alignment uses interpolation to obtain data points at higher frame rates, and the time-aligned data is compounded to increase the SNR.

25 Claims, 12 Drawing Sheets

(56) References Cited

U.S. PATENT DOCUMENTS

| | | |
|---|---|---|
| 2017/0333005 A1 | 11/2017 | Chen et al. |
| 2019/0076126 A1 | 3/2019 | Greenleaf et al. |
| 2021/0169455 A1* | 6/2021 | Annangi ............... A61B 8/54 |
| 2021/0174496 A1* | 6/2021 | Annangi ............. A61B 8/5223 |
| 2024/0248206 A1* | 7/2024 | Lee ..................... G01S 15/8995 |

OTHER PUBLICATIONS

Capriotti, Margherita, James Greenleaf, and Matthew W. Urban. "A time-aligned plane wave compounding method for high frame rate shear wave elastography." The Journal of the Acoustical Society of America 148.4_Supplement (2020): 2447-2447. (Year: 2020).*

Song, Pengfei, et al. "Fast shear compounding using robust 2-D shear wave speed calculation and multi-directional filtering." Ultrasound in medicine & biology 40.6 (2014): 1343-1355. (Year: 2014).*

Song, Pengfei, et al. "Two-dimensional shear-wave elastography on conventional ultrasound scanners with time-aligned sequential tracking (TAST) and comb-push ultrasound shear elastography (CUSE)." IEEE transactions on ultrasonics, ferroelectrics, and frequency control 62.2 (2015): 290-302. (Year: 2015).*

Apostolakis, I. et al., Pulse Wave Imaging Using Coherent Compounding in a Phantom and In Vivo, Physics in Medicine & Biology, 2017, 62(5):1700-1730.

Bae, S. et al., Enhanced Shear Wave Elastography for HIFU Monitoring of Stiff Uterine Fibroids, 2018 IEEE International Ultrasonics Symposium, 3 pages.

Benane, Y. et al., Experimental Implementation of a Pulse Compression Technique Using Coherent Plane-Wave Compounding, IEEE Transactions on Ultrasonics, Ferroelectrics, and Frequency Control, 2018, 65(6):1025-1036.

Bercoff, J. et al., Supersonic Shear Imaging: A New Technique for Soft Tissue Elasticity Mapping, IEEE Transactions on Ultrasonics, Ferroelectrics, and Frequency Control, 2004, 51(4):396-409.

Bercoff, J. et al., Ultrafast Compound Doppler Imaging: Providing Full Blood Flow Characterization, IEEE Transactions on Ultrasonics, Ferroelectrics, and Frequency Control, 2011, 58(1):134-147.

Capriotti, M. et al., Time-Aligned Plane Wave Compounding Methods for High-Frame-Rate Shear Wave Elastography: Experimental Validation and Performance Assessment on Tissue Phantoms, Ultrasound in Medicine and Biology, 2021, 47(7):1931-1948.

Demene, C. et al., Spatiotemporal Clutter Filtering of Ultrafast Ultrasound Data Highly Increases Doppler and fUltrasound Sensitivity, IEEE Transactions on Medical Imaging, 2015, 34(11):2271-2285.

Errico, C. et al., Ultrafast Ultrasound Localization Microscopy for Deep Super-Resolution Vascular Imaging, Nature, 2015, 527(7579):499-502.

Gennisson, J. et al., 4-D Ultrafast Shear-Wave Imaging, IEEE Transactions on Ultrasonics, Ferroelectrics, and Frequency Control, 2015, 62(6):1059-1065.

Gong, P. et al., Delay-Encoded Harmonic Imaging (DE-HI) in Multiplane-Wave Compounding, IEEE Transactions on Medical Imaging, 2017, 36(4):952-959.

Hasnain, S. et al., A Novel Two-Dimensional Displacement Estimation for Angled Shear Wave Elastography, 2019 IEEE International Ultrasonics Symposium (IUS), pp. 1383-1386.

Hollender, P. et al., Intracardiac Acoustic Radiation Force Impulse (ARFI) and Shear Wave Imaging in Pigs with Focal Infarctions, IEEE Transactions on Ultrasonics, Ferroelectrics, and Frequency Control, 2013, 60(8):1669-1682.

Kang, J. et al., High PRF Ultrafast Sliding Compound Doppler Imaging: Fully Qualitative and Quantitative Analysis of Blood Flow, Physics in Medicine & Biology, 2018, 63:045004, 16 pages.

Montaldo, G. et al., Coherent Plane-Wave Compounding for Very High Frame Rate Ultrasonography and Transient Elastography, IEEE Transactions on Ultrasonics, Ferroelectrics, and Frequency Control, 2009, 56(3):489-506.

Provost, J. et al., 3D Ultrafast Ultrasound Imaging In Vivo, Physics in Medicine & Biology, 2014, 59:L1-L13.

Provost, J. et al., 3-D ultrafast Doppler Imaging Applied to the Noninvasive Mapping of Blood Vessels In Vivo, IEEE Transactions on Ultrasonics, Ferroelectrics, and Frequency Control, 2015, 62(8):1467-1472.

Salles, S. et al., Experimental Evaluation of Spectral-Based Quantitative Ultrasound Imaging Using Plane Wave Compounding, IEEE Transactions on Ultrasonics, Ferroelectrics, and Frequency Control, 2014, 61(11):1824-1834.

Saris, A. et al., A Comparison Between Compounding Techniques Using Large Beam-Steered Plane Wave Imaging for Blood Vector Velocity Imaging in a Carotid Artery Model, IEEE Transactions on Ultrasonics, Ferroelectrics, and Frequency Control, 2016, 63(11):1758-1771.

Sarvazyan, A. et al., Acoustic Waves in Medical Imaging and Diagnostics, Ultrasound in Medicine & Biology, 2013, 39(7):1133-1146.

Schiefler Jr., N. et al., Generation and Analysis of Ultrasound Images Using Plane Wave and Sparse Arrays Techniques, Sensors, 2018, 18:3660, 23 pages.

Song, P. et al., Shear Wave Elastography on the GE LOGIQ E9 with Comb-push Ultrasound Shear Elastography (CUSE) and Time Aligned Sequential Tracking (TAST), 2014 IEEE International Ultrasonics Symposium Proceedings, pp. 1101-1104.

Song, P. et al., Two-Dimensional Shear-Wave Elastography on Conventional Ultrasound Scanners with Time-Aligned Sequential Tracking (TAST) and Comb-push Ultrasound Shear Elastography (CUSE), IEEE Transactions on Ultrasonics, Ferroelectrics, and Frequency Control, 2015, 62(2):290-302.

Tanter, M. et al., Ultrafast Imaging in Biomedical Ultrasound, IEEE Transactions on Ultrasonics, Ferroelectrics, and Frequency Control, 2014, 61(1):102-119.

Tiran, E. et al., Multiplane Wave Imaging Increases Signal-to-Noise Ratio in Ultrafast Ultrasound Imaging, Physics in Medicine & Biology, 2015, 60:8549-8566.

PCT International Search Report and Written Opinion, PCT/US2021/049040, Nov. 30, 2021, 15 pages.

* cited by examiner

TIME-ALIGNED PLANE WAVE COMPOUNDING OF ULTRASOUND DATA

CROSS-REFERENCE TO RELATED APPLICATIONS

This application represents the national stage entry of PCT/US2021/049040 filed on Sep. 3, 2021 and claims the benefit of U.S. Provisional Patent Application Ser. No. 63/075,064, filed on Sep. 4, 2020, and entitled "TIME-ALIGNED PLANE WAVE COMPOUNDING OF ULTRASOUND DATA," the contents of which is herein incorporated by reference in its entirety.

STATEMENT REGARDING FEDERALLY SPONSORED RESEARCH

This invention was made with government support under HL145268 awarded by the National Institutes of Health. The government has certain rights in the invention.

BACKGROUND

Shear wave elastography ("SWE") is an ultrasonic technique able to quantitatively assess the mechanical properties of tissues, combining acoustic radiation force and ultrafast imaging. While utilizing coherent plane wave compounding enhances signal-to-noise ratio ("SNR"), it also reduces the effective pulse repetition frequency ("$PRF_e$"), affecting the accuracy of the motion and, consequently, of the material properties. It is important to maintain both a high SNR and $PRF_e$, particularly for the characterization of (material and/or geometrical) dispersive tissues.

Plane wave imaging ("PWI") has been developed and utilized over the last decade for many applications. One of the primary benefits of plane wave imaging is the high frame rates that can be achieved. However, using unfocused plane wave transmits leads to a reduction in ultrasound echo SNR. One approach to improve the SNR using PWI is to use multiple angled plane wave transmissions, then the received echoes are coherently summed, or compounded in a technique known as plane wave compounding ("PWC"). In addition, diverging waves can be used for certain transducer configurations in similar ways to plane waves. Other approaches for increasing the SNR such as coded excitation and multiplane transmissions have also been used.

Shear wave elastography uses focused ultrasound beams to generate acoustic radiation force ("ARF") to generate a propagating shear wave. Plane wave imaging or other approaches are then used to measure the shear wave propagation with high effective frame rates in the kilohertz range. PWC can be employed to improve the SNR and spatial coverage of reliable shear wave velocity values. Both time-of-flight ("TOE") and Fourier-based techniques have improved performance with higher frame rates. With the TOF methods, a group velocity, or velocity of the wave packet, is estimated from time-domain data. In the Fourier-based techniques, the spatiotemporal data (x-t) are commonly transformed into a frequency domain with spatial and temporal frequency axes (k-f) to evaluate phase velocities, or the velocity of a wave at a particular frequency. However, the frame rate has to be balanced with echo SNR, which has a strong effect on the quality of shear wave motion estimates and resulting shear wave velocity measurements.

The temporal resolution for shear wave elastography is particularly important in applications with tissues with increased stiffness (i.e., higher shear wave velocity), such as skeletal muscle, tendons, ligaments, and arteries. Additionally, for the characterization of viscoelastic or dispersive materials, high frequency bandwidth is desirable.

SUMMARY OF THE DISCLOSURE

The present disclosure addresses the aforementioned drawbacks by providing a method for generating a time series of images with an ultrasound system. Ultrasound data are acquired from a region-of-interest using an ultrasound system. The ultrasound data are acquired using a series of angled wave emissions over a duration of time such that the ultrasound data include angular view data for each of a plurality of temporal sample points. Temporally aligned ultrasound data are generated by interpolating the ultrasound data along the temporal domain, thereby generating additional angular view data at each temporal sample point. A time series of images is generated from the temporally aligned ultrasound data by compounding the angular view data at each temporal sample point, thereby generating an image at each time point corresponding to each temporal sample point.

It is another aspect of the present disclosure to provide a method for generating a time series of images with an ultrasound system. Ultrasound data are acquired from a region-of-interest using an ultrasound system. The ultrasound data are acquired using a series of angled wave emissions over a duration of time such that the ultrasound data include angular view data for each of a plurality of temporal sample points. Temporally aligned ultrasound data are generated by interpolating the ultrasound data along the temporal domain, thereby generating additional angular view data at each temporal sample point. A time series of images is generated from the temporally aligned ultrasound data using a sliding window average of angular view data along the temporal dimension in order to generate an image frame for each of a plurality of different time points each corresponding to a different temporal position of the sliding window.

It is another aspect of the present disclosure to provide a method for generating a time series of images with an ultrasound system. Ultrasound echo signal data are acquired from a region-of-interest using an ultrasound system. The ultrasound echo signal data are acquired using a series of angled wave emissions over a duration of time such that the ultrasound echo signal data include angular view data for each of a plurality of temporal sample points. Motion data are estimated from the ultrasound echo signal data. The motion data indicate shear wave motion occurring in the region-of-interest when the ultrasound echo signal data were acquired. Temporally aligned motion data are generated by interpolating the motion data along the temporal domain, thereby generating additional angular view data at each temporal sample point. A time series of images is generated from the temporally aligned motion data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIGS. 6A-6E show image acquisition schemes for traditional PWC (FIG. 6A); full PWC (FIG. 6B); PWC MA (FIG. 6C); TA $PWC_{IQ}$ (FIG. 6D); and TA $PWC_{vm}$ (FIG. 6E), where $n_i$ are the time samples; $n_{vi}$ is the $i^{th}$ plane wave image, captured at the $i^{th}$ view, color coded for each different angle; the black circles are the interpolated data between adjacent $n_{vi}$, at each corresponding time sample; $F_i$ is the $i^{th}$ retrieved frame. For all the PWC modalities, $N_v$=5.

DETAILED DESCRIPTION

Described here are systems and methods for performing shear wave elastography and/or other ultrasound imaging procedures, in which data are acquired with high SNR while maintaining a high $PRF_e$, using conventional clinical ultrasound scanners. For example, in addition to shear wave elastography, the systems and methods described in the present disclosure can be used to image or otherwise measure tissue motion other than shear waves, including tissue motion from acoustic radiation force, tissue motion from mechanical actuation, endogenous tissue motion (e.g., pulsation), and blood flow. In general, ultrasound data are acquired using a plane waves at different angles, after which a time alignment process is applied to the acquired data. The time alignment uses interpolation to obtain data points at higher frame rates, and the time-aligned data is compounded to increase the SNR.

Thus, in some embodiments described in the present disclosure, ultrasound data are effectively interpolated for all angled plane wave acquisitions to create a data set that has ultrasound or motion samples for each plane wave acquisition and temporal sample. This technique may be referred to as time-aligned plane wave compounding ("TA PWC"). Additionally or alternatively, a PWC moving average ("MA") technique can also be implemented. These TA PWC methodologies can be applied to areas of biomedical ultrasound where high frame rate is necessary, but echo SNR may be diminished. This includes Doppler imaging including microvascular flow and super-resolution imaging. Additionally, pulse wave imaging or imaging of other tissue motion could also benefit from these techniques. These techniques could also be used with coded excitation and multi-plane wave transmissions with coding approaches.

Figure 1A:
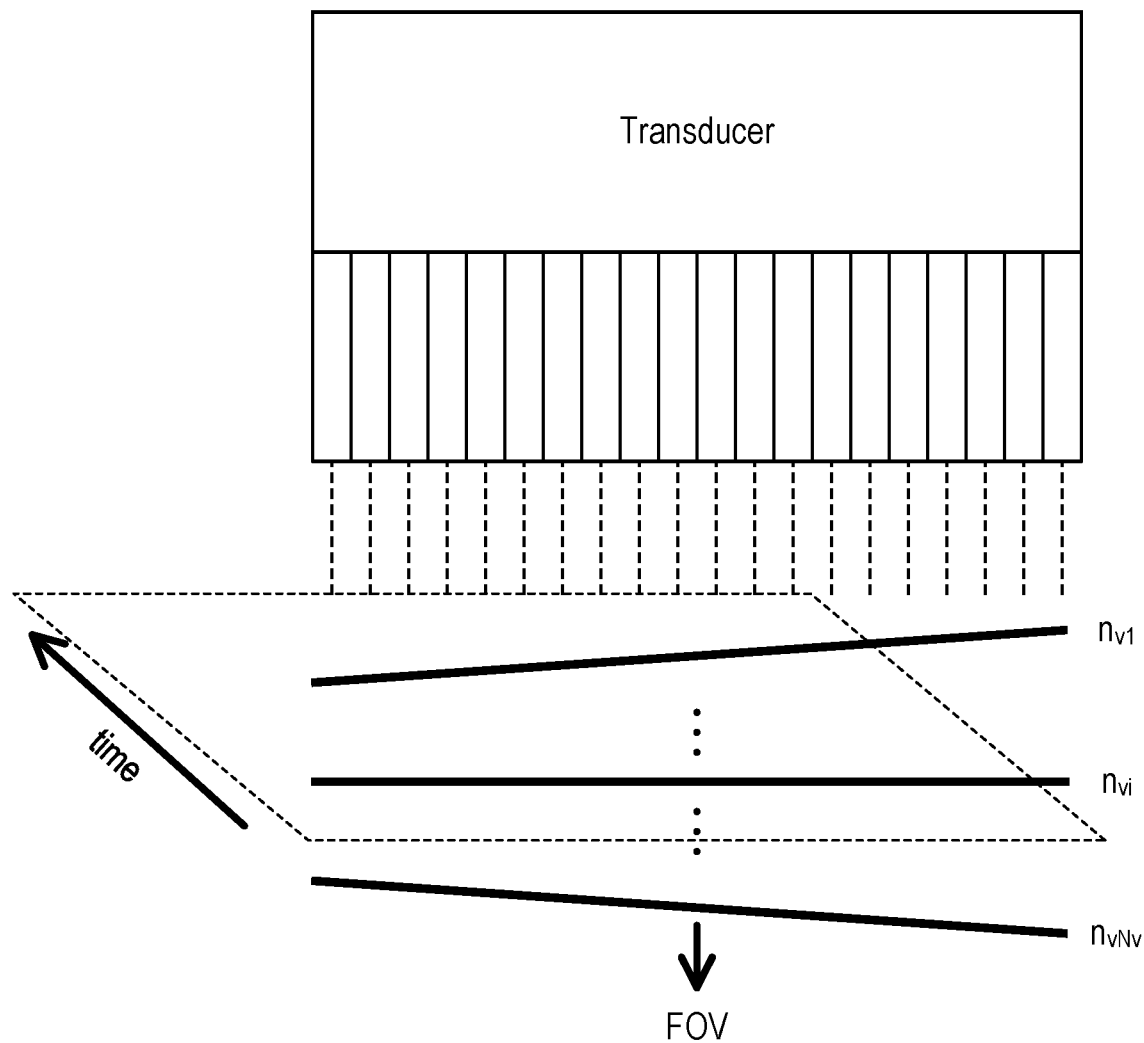
FIGS. 1A and 1B show an example scheme of traditional plane wave compounding (PWC) imaging: Ultrasonic acquisition in space and time is shown in FIG. 1A and the corresponding image formation is shown in FIG. 1B, where $n_i$ are the time samples; $n_{vi}$ is the $i^{th}$ plane wave image, captured at the $i^{th}$ view, color coded for each different angle; $F_i$ is the $i^{th}$ retrieved frame. The example of using five views is shown.

In general, plane wave imaging techniques are capable of capturing a full field-of-view ("FOV") in a much faster way than sequential line scanning, which can allow for imaging of dynamic events at high frame rates. The lower ultrasound pressure due to the emission of a plane wave, rather than a focused beam for sequential line or volume scanning, can be compensated for by the coherent compounding of a number of views, $N_v$, that have been successively acquired in the same way, orienting the plane wave at $\theta_i$ angles. The working principle of a general PWI technique is illustrated in FIG. 1A.

Figure 1B:
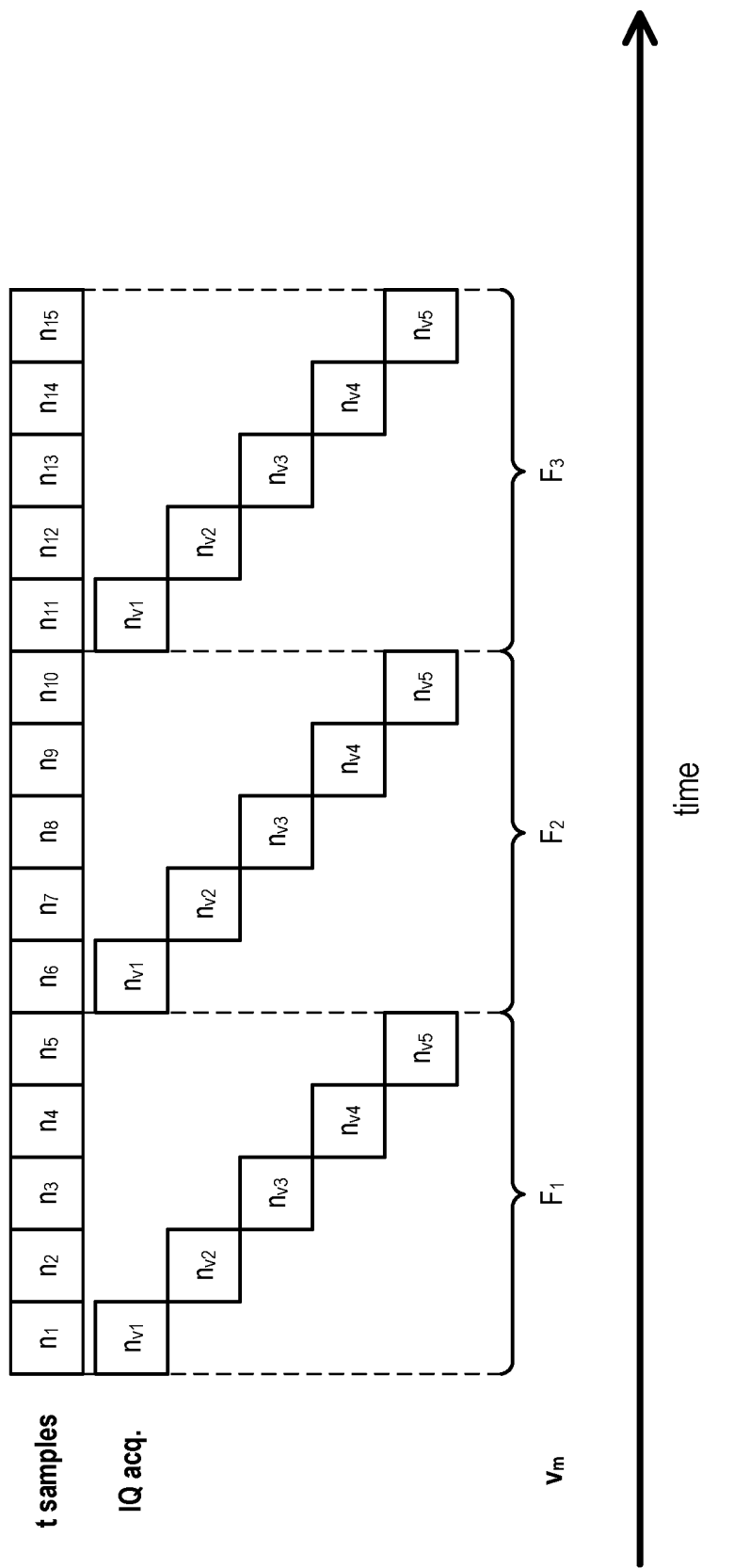

FIG. 1B summarizes the image formation along the evolution of time. In this process, each frame from angle $\theta_i$ is compounded after acquiring the last of the $N_v$ views. The signal level of the image results as a coherent average of the $N_v$ views, enhancing the consistent elements in the FOV and averaging out unbiased noise, hence providing a higher SNR, particularly as the SNR is proportional to the square root of $N_v$. In shear wave elastography applications, during the acquisition of the $N_v$ views, or frames, a shear wave will move and the reconstructed motion will be an average of the captured motion in each nth view. This effect will be more detrimental in stiffer materials with higher shear wave velocity. The effective frame rate, $PRF_e$, of the acquired dataset will be reduced $N_v$ times with respect to PWI with $N_v$=1.

$$PRF_e = \frac{PRF}{N_v}; \quad (1)$$

where PRF is the pulse repetition frequency. Similar reductions in the effective frame rate may be observed for other tissues motions as well, including tissue motion from acoustic radiation force, tissue motion from mechanical actuation, endogenous tissue motion (e.g., pulsation of vessels), and blood flow. To recover the loss in $PRF_e$, the systems and methods described in the present disclosure utilize a time-aligned plane wave compounding technique that exploits interpolation in the time-domain and compounding of the angular views in the spatial domain (e.g., the 2D spatial domain).

In the conventional, full PWC method, acquisitions are performed at the full frame rate for each nth view. The angle at which the view is oriented is changed after acquiring the event for the entire observation period. This approach requires the full acquisition time to be extended by $N_v$ times and assumes the event to be repeatable.

Figure 2A:
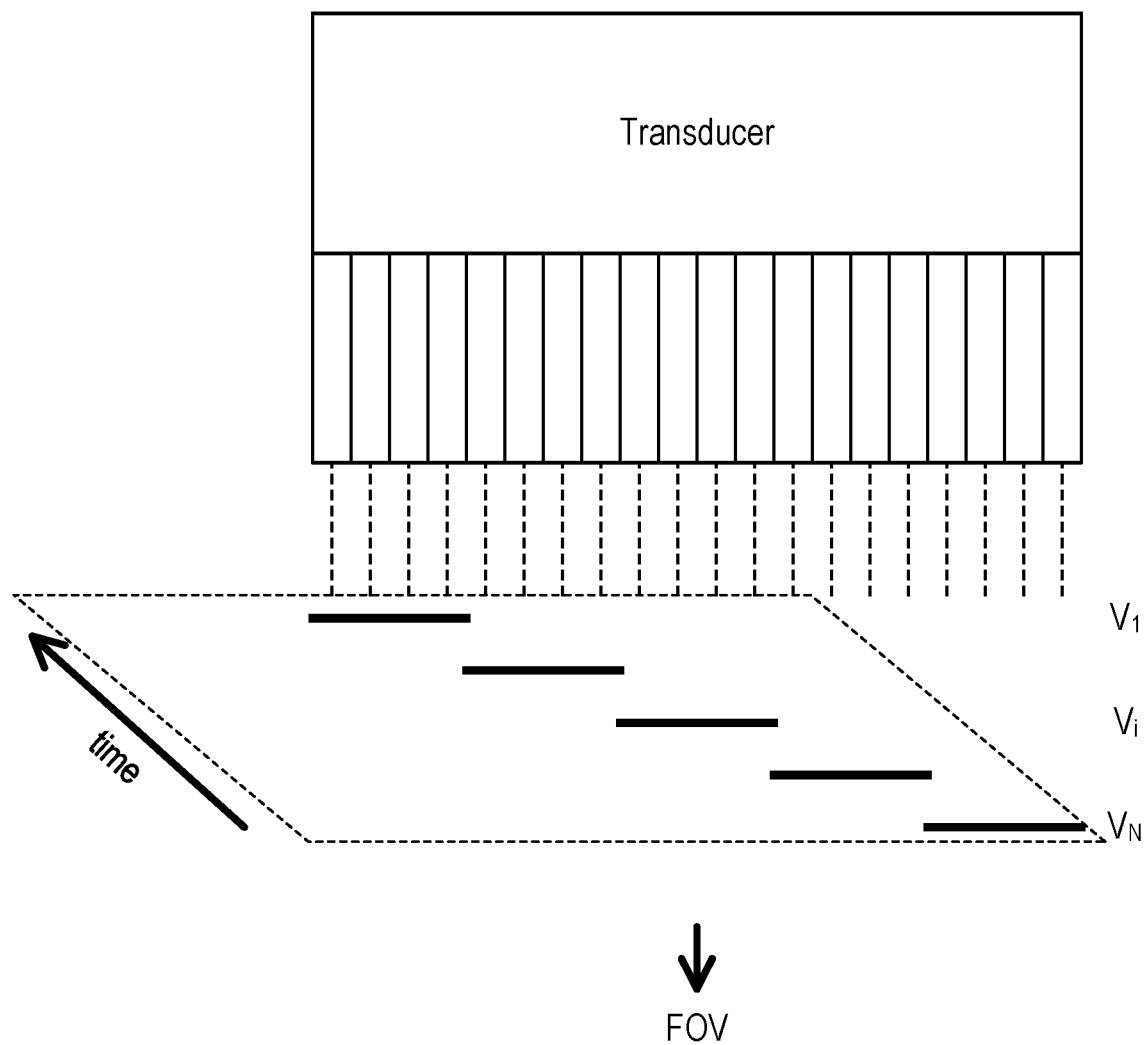
FIGS. 2A and 2B show an example scheme of time-aligned sequential tracking imaging. Ultrasonic acquisition in space and time is shown in FIG. 2A and the corresponding image formation is shown in FIG. 2B, where $V_i$ is the $i^{th}$ vector in the FOV; the black circles are the interpolated data between consecutive $V_i$ vectors, at each corresponding time sample; $FOV_i$ is the $i^{th}$ retrieved FOV. The example of using five vectors is shown.
Figure 2B:
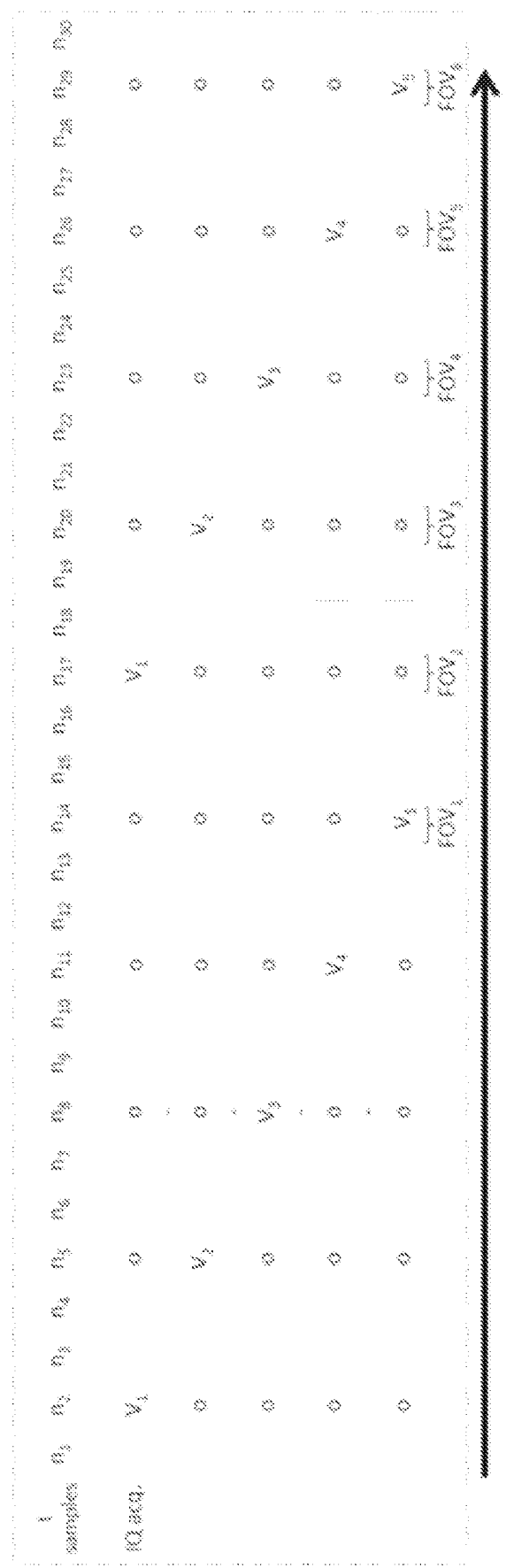

As one non-limiting example, temporal alignment of the acquired ultrasound data samples can be implemented using an adapted time-aligned sequential tracking ("TAST") algorithm. A conventional TAST algorithm is illustrated with respect to FIGS. 2A and 2B. As shown, separate lines or vectors are scanned in a sequential fashion for a finite number of vectors. Not every spatial location is fully sampled through time, however, so the shear wave motion for the vectors are instead interpolated such that the resulting data is sampled at the PRF value. These interpolated values are depicted as open circles in FIG. 2B.

Figure 3A:
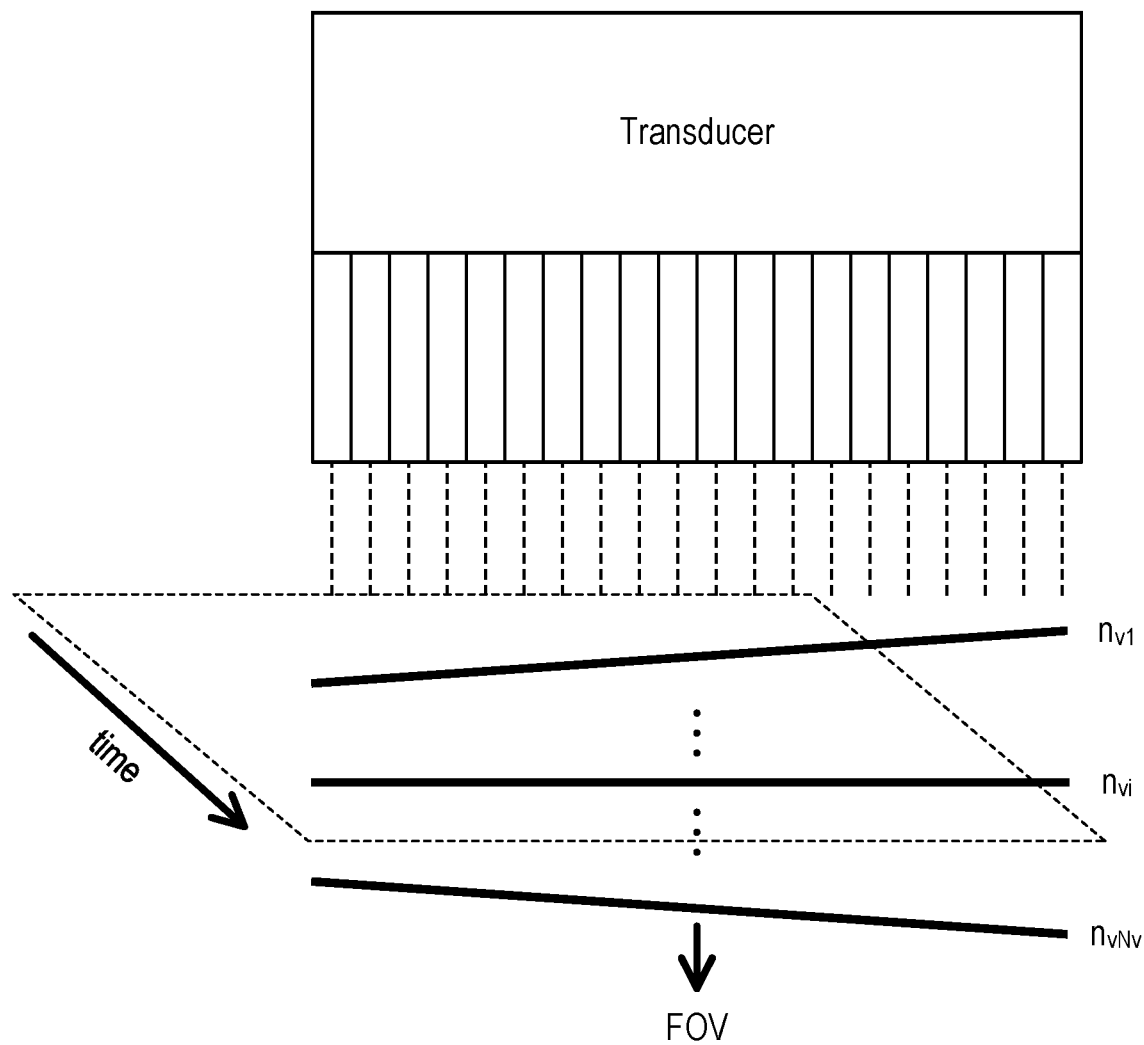
FIGS. 3A and 3B show an example scheme of time-aligned plane wave compounding (TA PWC). Ultrasonic acquisition in space and time is shown in FIG. 3A and the corresponding image formation is shown in FIG. 3B, where $n_i$ are the time samples; $n_{vi}$ is the $i^{th}$ plane wave image, captured at the $i^{th}$ view, color coded for each different angle; the black circles are the interpolated data between adjacent $n_{vi}$, at each corresponding time sample; $F_i$ is the $i^{th}$ retrieved frame. The example of using 5 views is shown.
Figure 3B:
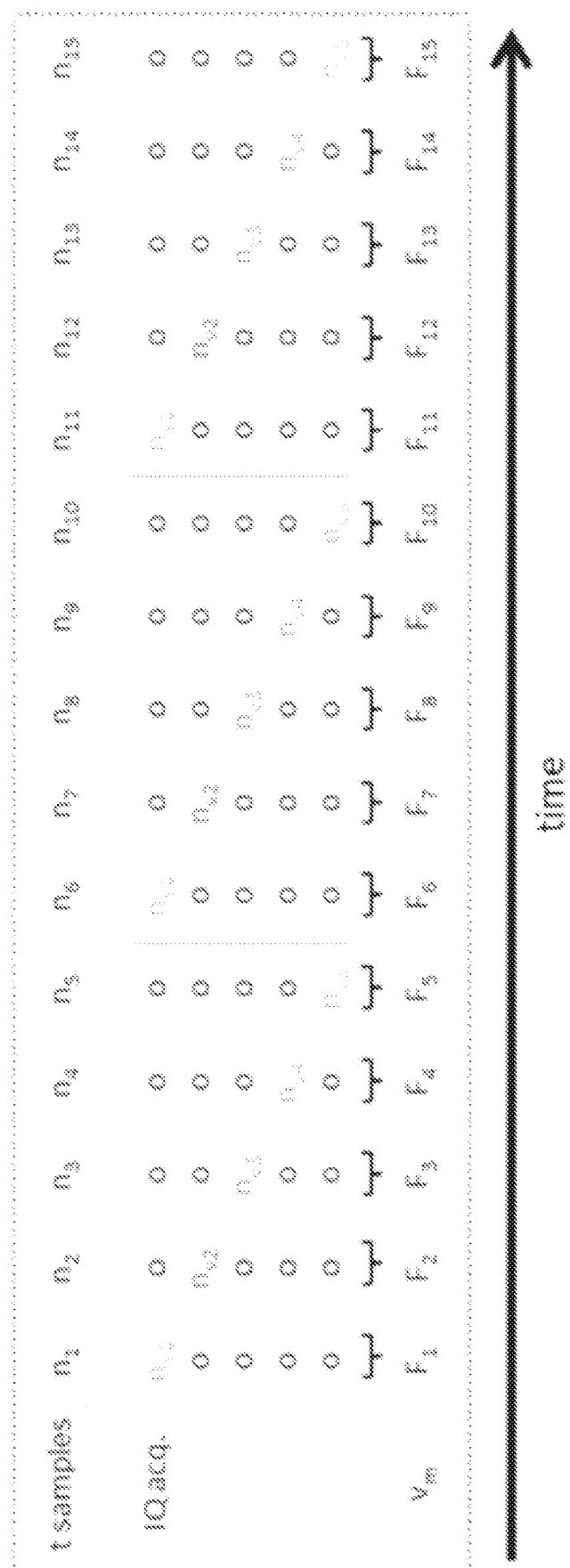

As mentioned, the TAST algorithm can be adapted for use with PWC-based acquisitions. As shown in FIGS. 3A and 3B, the resulting TA PWC method generally utilizes interpolation in time of each acquired nth view, to recover data with $PRF_e = PRF$, and makes use of spatial compounding across N images in order to enhance image quality of the whole FOV. The interpolated values are depicted as open circles in FIG. 3B. It should be noted that in the original TAST implementation, the shear wave motion was interpolated and not the original ultrasound data.

Figure 4A:
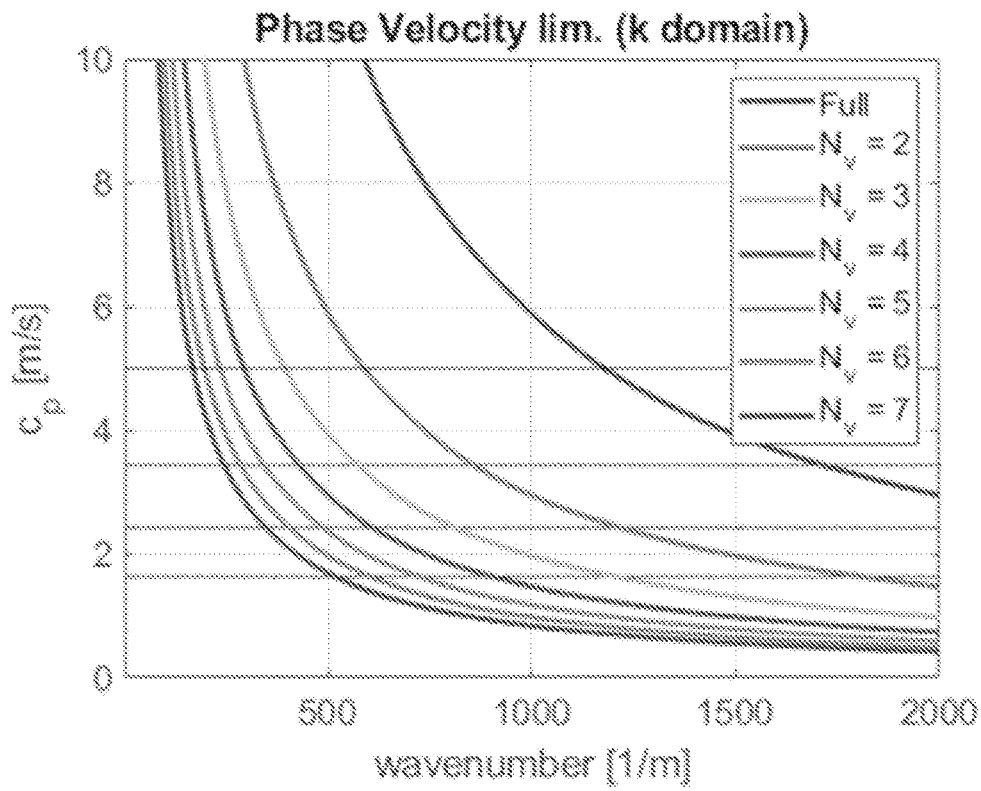
FIGS. 4A and 4B show theoretical frequency—wavenumber limits for increased number of views used in PWC, in terms of phase velocity (FIG. 4A) for phantoms of increasing shear wave velocity and theoretical maximum wavenumber (FIG. 4B) for a phantom with E=45 kPa phantom ($c_s$=3.43 m/s), color coded for the total number of views used. Black lines=phantoms velocity.
Figure 4B:
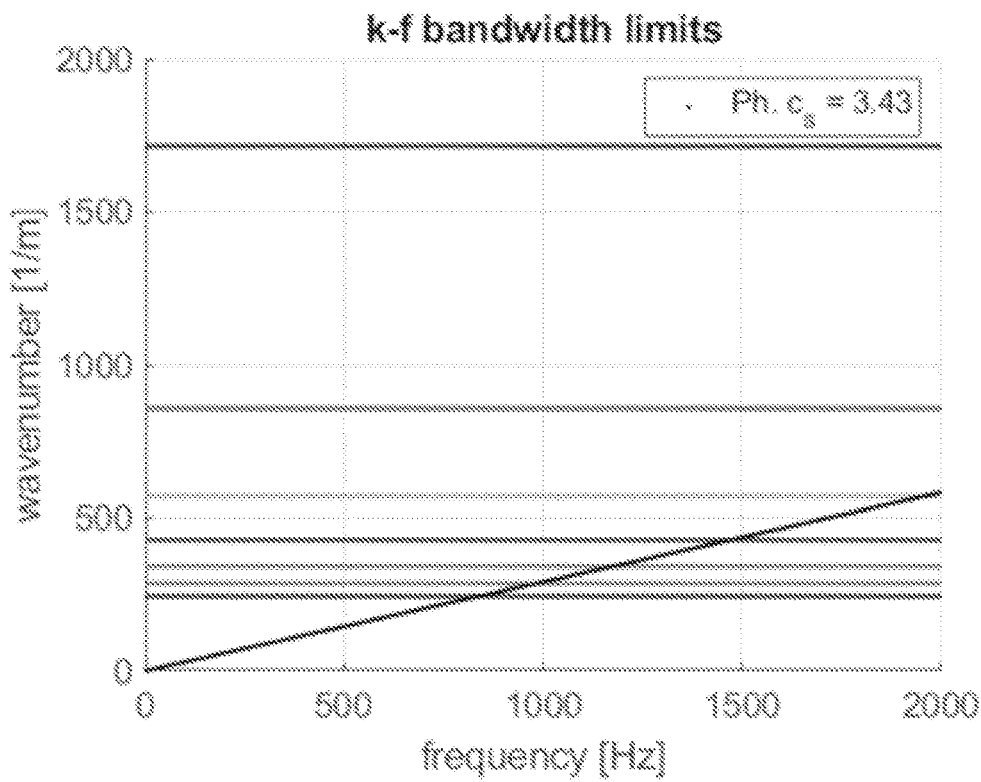

The advantage of having a high frame rate in SWE can be understood with reference to FIGS. 4A and 4B. FIG. 4A shows plots demonstrating the maximum frequency available for an increasing number of views, $N_v$ (hence, decreasing $PRF_e$), translated in phase velocity limits as:

$$f_{max} = \frac{f_s}{2} = \frac{PRF_e}{2}; \quad (2)$$

$$c_{p,max} = \frac{f_{max}}{k_i}; \quad (3)$$

where $f_s$ is the sampling frequency calculated as $f_s = 1/T_{acq}$ (in the example shown in FIG. 4A, $T_{acq} = 85$ μs, such that $f_s = 11.765$ kHz), $f_{max}$ is the maximum frequency that can be measured without being aliased, $k_i$ is every ith wavenumber value, and $c_{p,max}$ is the maximum velocity.

The different colors in FIG. 4A correspond to the number of views used, as shown in the legend of the figure. It can be noted how using a higher number of views would result in a much lower maximum retrievable velocity. This would particularly impact higher shear velocity values, which would be measured in stiffer tissues, provided the same wavenumber vector.

A similar evaluation can be done in terms of spatial frequency indicated by the wavenumber, as shown in FIG. 4B. Given a tissue with a certain wave velocity, the maximum wavenumber available, $k_{max}$, decreases drastically when using an increasing number of views, $N_v$, especially for higher shear wave velocities:

$$k_{max}(c_s) = \frac{f_{max}}{c_s}; \quad (4)$$

where $k_{max}(c_s)$ indicates the maximum wavenumber available, provided a given number of views, $N_v$ (color coded for each $N_v$ used, as in FIG. 4A). A line for a 45 kPa phantom of shear wave speed, $c_s = 3.43$ m/s, is shown by the black line: the intersection of such line with the maximum wavenumber line for each $N_v$ used provide the frequency and wavenumber limits available without incurring spatial aliasing. These theoretical relationships can be used to predict the available bandwidth and/or the number of views, $N_v$, to choose when estimating ranges of shear wave velocities for given phantoms. For example, FIG. 4B shows the frequency limits for a phantom with Young's modulus of E=45 kPa, with an estimated shear wave velocity of 3.43 m/s. If choosing an $N_v = 7$, the temporal and spatial frequency bandwidth would be limited at 836 Hz and 244 l/m, respectively. Choosing an $N_v = 3$ would extend the temporal and spatial frequency bandwidth to 1968 Hz and 574 l/m, respectively.

The values of 1.63, 2.42 and 3.43 m/s are group velocity values extracted for bulk phantoms of E=10, 25, and 45 kPa, respectively. The value of 5 m/s used is a minimum representative shear wave speed value in arterial tissue. At this wave speed the risk of incurring spatial and temporal aliasing is higher, but also the available k-f space to be used in the retrieval of phase velocity to characterize dispersive media is strongly reduced.

As mentioned above, in some alternative embodiments, the compounding of every $N_v$ images can be replaced with a moving average. This retains the averaging over $N_v$ angular views, but increases the $PRF_e$. As noted above, this adaptation can be referred to as a PWC MA technique.

Figure 5:
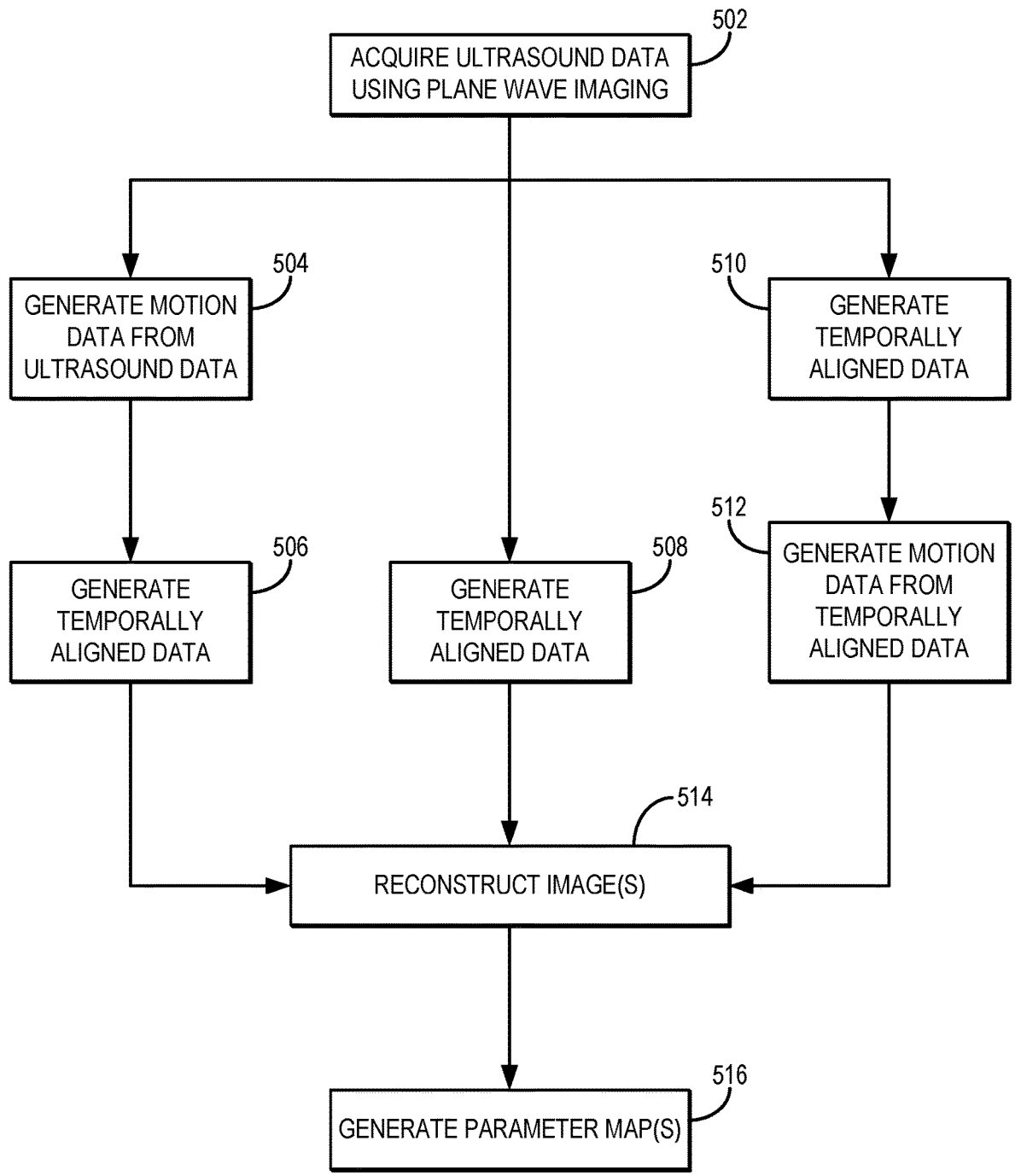
FIG. 5 is a flowchart setting forth the steps of an example method for time-aligned plane wave compounding with an ultrasound system.

Referring now to FIG. 5, a flowchart is illustrated as setting forth the steps of an example method for generating images with an ultrasound system using time-aligned plane wave compounding. The method includes acquiring ultrasound data using a series of angled plane wave emissions, such as may be used in plane wave imaging, as indicated at step 502. Alternatively, the ultrasound data may also be acquired using diverging waves with different virtual (i.e., negative) foci in similar ways to plane waves with different angles. In this way, the ultrasound data includes data samples for a plurality of different angled waves in addition to a plurality of different time points. In some instances, the ultrasound data are acquired following, or concurrent with, tissue motion occurring in a region-of-interest, such as a region in a subject containing one or more tissues under examination. Thus, in some embodiments, the ultrasound data may be motion data indicative of underlying tissue motion occurring in an imaged region. In some embodiments, the tissue motion may be shear wave motion associated with one or more shear waves that are being induced in the region-of-interest while the ultrasound data are acquired. In other embodiments, the tissue motion may be induced in the region-of-interest using an acoustic radiation force, mechanical actuation, or the like, while the ultrasound data are acquired. In some other embodiments, the tissue motion may be endogenous tissue motion occurring in the region-of-interest while the ultrasound data are acquired, such as endogenous pulsations and/or blood flow.

For instance, in some implementations, the acquired ultrasound data may include motion data that have been estimated from ultrasound echo signal data and are, therefore, indicative of tissue motion occurring in the region-of-interest from which the ultrasound echo signal data were acquired. In these instances, the acquired ultrasound data can include the motion data. In other implementations, the motion data can be computed or otherwise estimated from the acquired ultrasound data. The motion data can include displacement data (e.g., particle displacement data), velocity data (e.g., particle velocity data), and/or acceleration data (e.g., particle acceleration data).

As shown in FIG. 5, the ultrasound data can be processed in a number of different ways. In one example, motion data can be computed or otherwise estimated from the acquired ultrasound data, as indicated at step 504 and then these motion data can be temporally aligned, as indicated at step 506, before proceeding to image reconstruction. In another example, the ultrasound data can be temporally aligned, as indicated at step 508 before proceeding to image reconstruction. In still another example, the ultrasound data can be temporally aligned, as indicated at step 510 and then motion data can be generated from the temporally aligned motion data, as indicated at step 512, before proceeding to image reconstruction.

As one example, the ultrasound and/or motion data can be temporally aligned by performing an interpolation along the temporal dimension of the data. The interpolation can be, as one example, a spline interpolation. In some implementations, extrapolated points before and after the length of the acquired temporal samples in the ultrasound and/or motion data need not be excluded, since in most instances they will not affect the interpolation. Retaining these extrapolated points allows for compounding over a longer time vector, without loss. While the performance of the method using interpolated versus extrapolated data is identical, the very first acquired $N_v$ views are usually discarded, as they may retain undesirable effects from the push pulse that would otherwise affect the subsequent interpolation/extrapolation, enhancing artifacts (as indicated below).

In some embodiments, the ultrasound data may be radio frequency ("RF") data, or in-phase/quadrature ("IQ") data, such as may be commonly demodulated after acquisition. In these instances, the temporal alignment proceeds by interpolating these IQ data. In some other embodiments, the ultrasound data may be indicative of motion data. In some instances, then, the temporal alignment may proceed by interpolating motion data, such as particle velocity as retrieved after autocorrelation (e.g., 2D autocorrelation) with an axial window of pixels and a temporal window of frames (e.g., an axial window of 3 pixels and a temporal window of 2 frames).

Additionally or alternatively, the very first frame immediately after a shear wave (or other externally induced tissue motion) excitation can be kept. In those instances when the effect of the first frame compromises the motion estimation due to the high power of the push pulse (or other external motion source) used to generate the shear waves (or other tissue motion), the first frame can be removed before reconstructing motion.

From the temporally aligned data, one or more images can be produced by compounding the angular views in the temporally aligned data and/or using a sliding window average, as indicated at step 514. For instance, images can be produced using conventional beamforming and compounding techniques. Thus, in some embodiments described in the present disclosure, ultrasound data are effectively interpolated for all angled plane wave acquisitions to create a data set that has ultrasound or motion samples for each plane wave acquisition and temporal sample.

In some instances, parameter maps can be generated from the reconstructed image(s), as indicated at step 516. For example, when the reconstructed image(s) are representative of shear wave motion, one or more mechanical property maps may be generated from the reconstructed image(s) using techniques known to those skilled in the art.

Figure 6A:
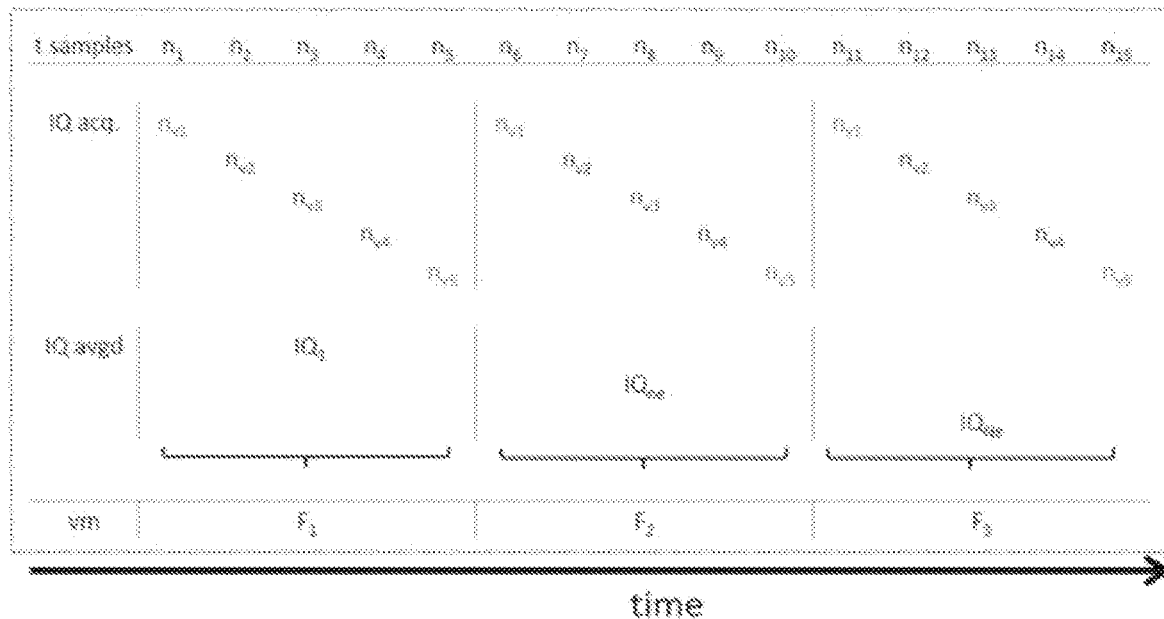
Figure 6B:
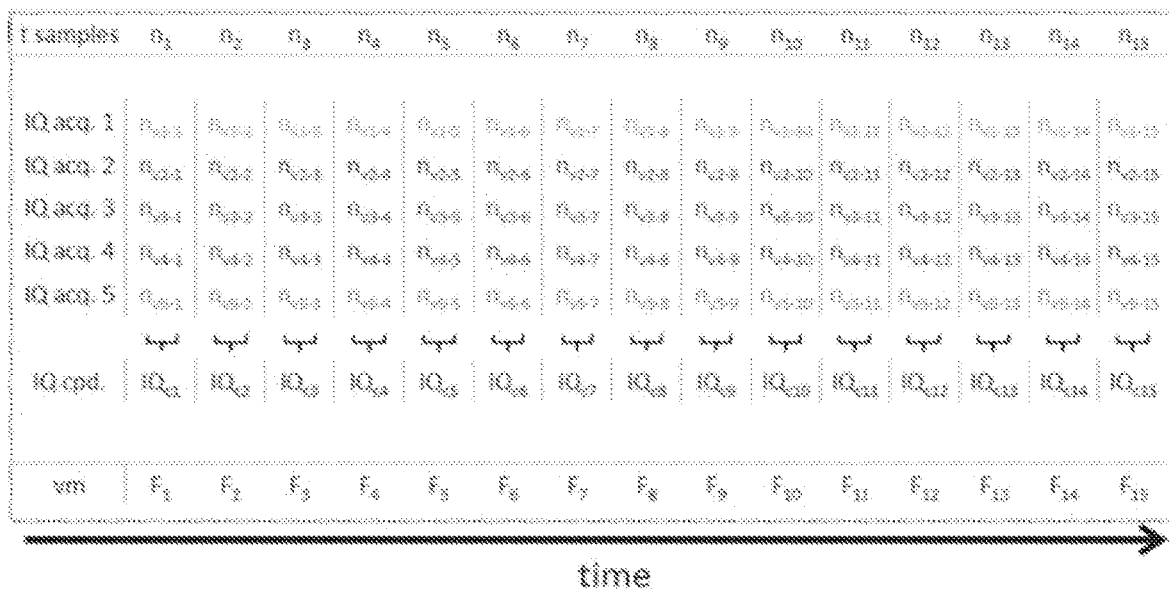
Figure 6C:
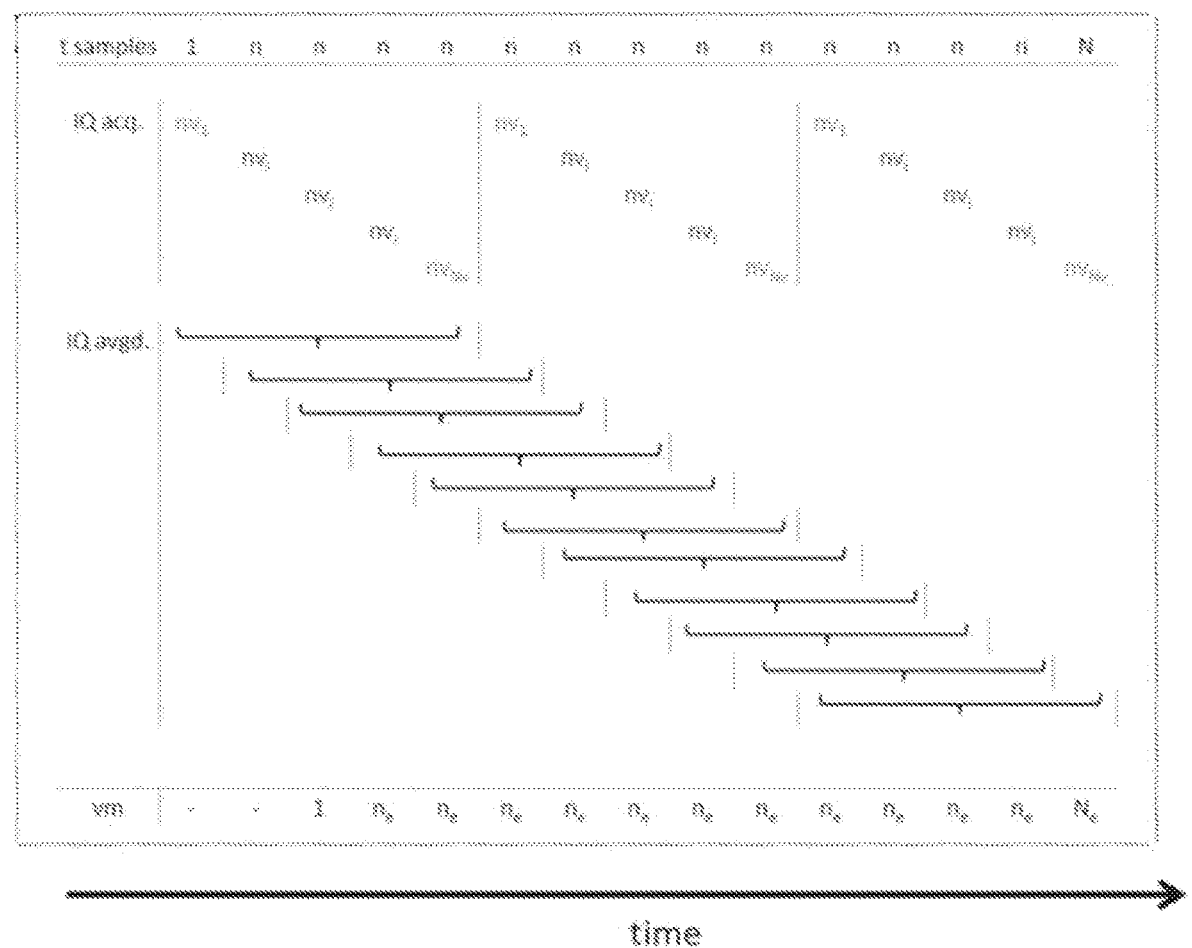
Figures 6D, 6E:
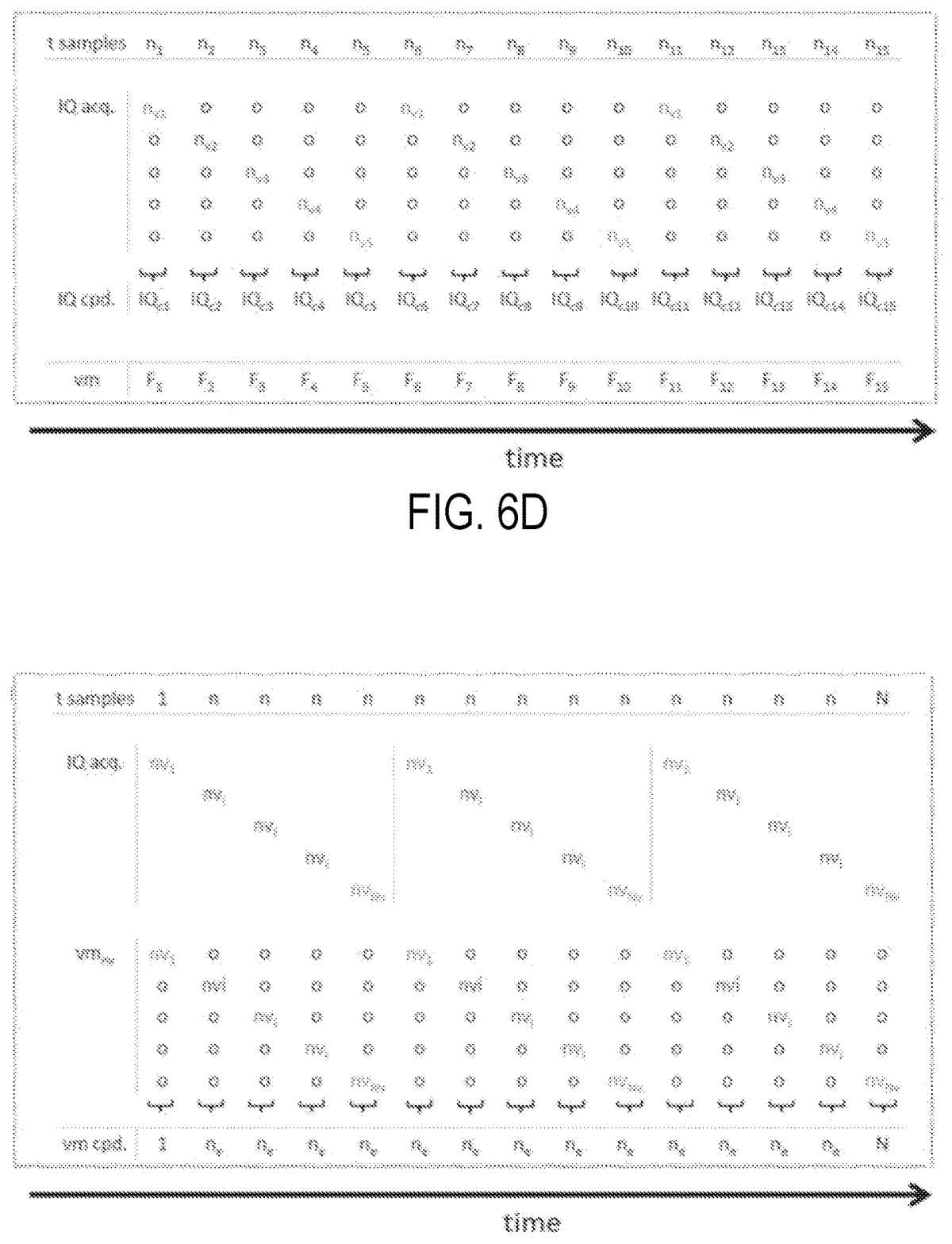

Referring to FIG. 6A, an example image acquisition scheme is shown for a traditional PWC method. Referring to FIG. 6B, an example image acquisition scheme is shown for a full PWC method. Referring to FIG. 6C, an example image acquisition scheme is shown for a PWC MA method. Referring to FIG. 6D, an example image acquisition scheme is shown for a TA-PWC method based on IQ data. Referring to FIG. 6E, an example image acquisition scheme is shown for a TA-PWC method based on particle velocity data. In these examples, $n_i$ are the time samples; $n_{vi}$ is the ith plane wave image, captured at the ith view, color coded for each different angle; the black circles are the interpolated data between adjacent $n_{vi}$, at each corresponding time sample; and $F_i$ is the ith retrieved frame. For all the PWC modalities in these examples, $N_v=5$.

Further utilizations of the TA-PWC and PWC MA can be applied to data acquired for the purposes of evaluating other physiological processes that require high frame rates and echo SNR, including but not limited to Doppler blood flow imaging of large vessels and microvessels. In addition, TA-PWC and PWC MA could be utilized for imaging of tissue motion and motion of ultrasound contrast agents for super-resolution imaging applications.

Figure 7:
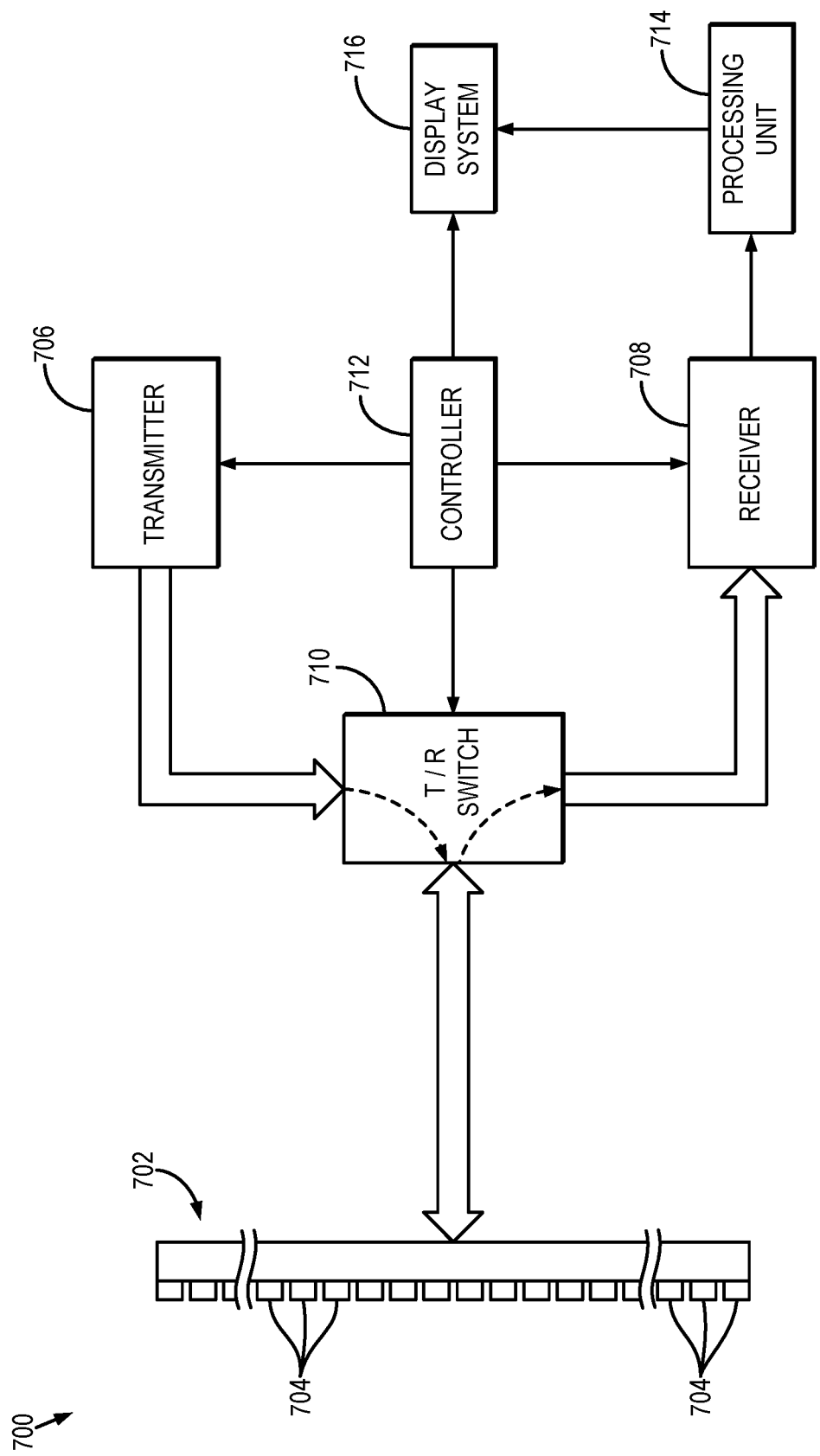
FIG. 7 is a block diagram of an example ultrasound system that can implement the methods described in the present disclosure.

FIG. 7 illustrates an example of an ultrasound system 700 that can implement the methods described in the present disclosure. The ultrasound system 700 includes a transducer array 702 that includes a plurality of separately driven transducer elements 704. The transducer array 702 can include any suitable ultrasound transducer array, including linear arrays, curved arrays, phased arrays, and so on. Similarly, the transducer array 702 can include a 1 D transducer, a 1.5 D transducer, a 1.75 D transducer, a 2 D transducer, a 3 D transducer, and so on.

When energized by a transmitter 706, a given transducer element 704 produces a burst of ultrasonic energy. The ultrasonic energy reflected back to the transducer array 702 (e.g., an echo) from the object or subject under study is converted to an electrical signal (e.g., an echo signal) by each transducer element 704 and can be applied separately to a receiver 708 through a set of switches 710. The transmitter 706, receiver 708, and switches 710 are operated under the control of a controller 712, which may include one or more processors. As one example, the controller 712 can include a computer system.

The transmitter 706 can be programmed to transmit unfocused or focused ultrasound waves. In some configurations, the transmitter 706 can also be programmed to transmit diverged waves, spherical waves, cylindrical waves, plane waves, or combinations thereof. Furthermore, the transmitter 706 can be programmed to transmit spatially or temporally encoded pulses.

The receiver 708 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 706 and the receiver 708 can be programmed to implement a high frame rate. For instance, a frame rate associated with an acquisition pulse repetition frequency ("PRF") of at least 100 Hz can be implemented. In some configurations, the ultrasound system 700 can sample and store at least one hundred ensembles of echo signals in the temporal direction.

The controller 712 can be programmed to design and implement an imaging sequence using the techniques described in the present disclosure (e.g., using angled plane wave emissions), or as otherwise known in the art. In some embodiments, the controller 712 receives user inputs defining various factors used in the design of the imaging sequence.

A scan can be performed by setting the switches 710 to their transmit position, thereby directing the transmitter 706 to be turned on momentarily to energize transducer elements 704 during a single transmission event according to the selected imaging sequence. The switches 710 can then be set to their receive position and the subsequent echo signals produced by the transducer elements 704 in response to one or more detected echoes are measured and applied to the receiver 708. The separate echo signals from the transducer elements 704 can be combined in the receiver 708 to produce a single echo signal.

The echo signals are communicated to a processing unit 714, which may be implemented by a hardware processor and memory, to process echo signals or images generated from echo signals. As an example, the processing unit 714 can generate temporally aligned ultrasound data, from which images can be reconstructed using the methods described in the present disclosure. Images produced from the echo signals by the processing unit 714 can be displayed on a display system 716.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a time series of images with an ultrasound system, the method comprising:
   (a) acquiring ultrasound data from a region-of-interest using an ultrasound system, wherein the ultrasound data are acquired using a series of angled wave emissions over a duration of time such that the ultrasound data comprise angular view data for each of a plurality of temporal sample points;
   (b) generating temporally aligned ultrasound data by interpolating the ultrasound data along a temporal domain, thereby generating additional angular view data at each temporal sample point; and
   (c) generating a time series of images from the temporally aligned ultrasound data by compounding the angular view data at each temporal sample point, thereby generating an image at each time point corresponding to each temporal sample point.

2. The method of claim 1, wherein the temporally aligned ultrasound data are generated by interpolating the ultrasound data along the temporal domain using a spline interpolation.

3. The method of claim 1, wherein the ultrasound data comprise motion data indicative of tissue motion occurring in the region-of-interest and acquiring the ultrasound data comprises acquiring ultrasound echo signals with the ultrasound system and estimating the motion data from the ultrasound echo signals.

4. The method of claim 1, further comprising estimating motion data from the temporally aligned ultrasound data, the motion data being indicative of tissue motion occurring in the region-of-interest when the ultrasound data were acquired.

5. The method of claim 3, further comprising inducing the tissue motion in the region-of-interest prior to acquiring the ultrasound data.

6. The method of claim 5, wherein inducing the tissue motion includes applying a mechanical actuation to cause the tissue motion in the region-of-interest.

7. The method of claim 5, wherein the ultrasound data comprise particle velocity data generated using an autocorrelation with an axial window having a set number of pixels and a temporal window having a set number of frames.

8. The method of claim 1, wherein the angled wave emissions comprise angled plane wave emissions.

9. The method of claim 1, wherein the angled wave emissions comprise diverging waves with different virtual foci.

10. A method for generating a time series of images with an ultrasound system, the method comprising:
    (a) acquiring ultrasound data from a region-of-interest using an ultrasound system, wherein the ultrasound data are acquired using a series of angled wave emissions over a duration of time such that the ultrasound data comprise angular view data for each of a plurality of temporal sample points;
    (b) generating temporally aligned ultrasound data by interpolating the ultrasound data along a temporal domain, thereby generating additional angular view data at each temporal sample point; and
    (c) generating a time series of images from the temporally aligned ultrasound data using a sliding window average of angular view data along the temporal dimension in order to generate an image frame for each of a plurality of different time points each corresponding to a different temporal position of the sliding window.

11. The method of claim 10, wherein the temporally aligned ultrasound data are generated by interpolating the ultrasound data along the temporal domain using a spline interpolation.

12. The method of claim 10, wherein the ultrasound data comprise at least one of radio frequency (RF) data or in-phase/quadrature (IQ) data.

13. The method of claim 10, wherein the ultrasound data comprise motion data indicative of tissue motion occurring in the region-of-interest.

14. The method of claim 10, further comprising estimating motion data from the temporally aligned ultrasound data, the motion data being indicative of tissue motion occurring in the region-of-interest when the ultrasound data were acquired.

15. The method of claim 13, further comprising inducing the tissue motion in the region-of-interest prior to acquiring the ultrasound data.

16. The method of claim 15, wherein the tissue motion comprises shear waves induced in the region-of-interest prior to acquiring the ultrasound data.

17. The method of claim 15, wherein the ultrasound data comprise particle velocity data generated using an autocorrelation with an axial window having a set number of pixels and a temporal window having a set number of frames.

18. The method of claim 13, wherein the tissue motion is an endogenous tissue motion.

19. The method of claim 18, wherein the tissue motion includes endogenous pulsatile motion.

20. The method of claim 18, wherein the tissue motion includes blood flow.

21. The method of claim 10, wherein the angled wave emissions comprise angled plane wave emissions.

22. The method of claim 10, wherein the angled wave emissions comprise diverging waves with different virtual foci.

23. A method for generating a time series of images with an ultrasound system, the method comprising:
    (a) acquiring ultrasound echo signal data from a region-of-interest in which one or more shear waves are propagating using an ultrasound system, wherein the ultrasound echo signal data are acquired using a series of angled wave emissions over a duration of time such that the ultrasound echo signal data comprise angular view data for each of a plurality of temporal sample points;
    (b) estimating motion data from the ultrasound echo signal data, the motion data being indicative of shear wave motion occurring in the region-of-interest when the ultrasound echo signal data were acquired;

(c) generating temporally aligned motion data by interpolating the motion data along a temporal domain, thereby generating additional motion data at each temporal sample point; and (d) generating a time series of images from the temporally aligned motion data.

24. The method of claim 23, wherein the time series of images is generated from the temporally aligned motion data by compounding the angular view data at each temporal sample point, thereby generating an image at each time point corresponding to each temporal sample point.

25. The method of claim 23, wherein the time series of images is generated from the temporally aligned motion data using a sliding window average of motion data along the temporal dimension in order to generate an image frame for each of a plurality of different time points each corresponding to a different temporal position of the sliding window.

\* \* \* \* \*

UNITED STATES PATENT AND TRADEMARK OFFICE
CERTIFICATE OF CORRECTION

| | | Page 1 of 1 |
|---|---|---|
| PATENT NO. | : 12,352,855 B2 | |
| APPLICATION NO. | : 18/044185 | |
| DATED | : July 8, 2025 | |
| INVENTOR(S) | : Matthew W. Urban et al. | |

It is certified that error appears in the above-identified patent and that said Letters Patent is hereby corrected as shown below:

In the Specification

Column 1, Line 54, "("TOE")" should be --("TOF")--.

Signed and Sealed this
Twenty-first Day of October, 2025

John A. Squires
*Director of the United States Patent and Trademark Office*